(12) United States Patent
Takehara

(10) Patent No.: US 6,598,288 B1
(45) Date of Patent: Jul. 29, 2003

(54) ARMATURE OF MOTOR, MANUFACTURING METHOD OF THE SAME AND MOTOR USING THE SAME AND MOTOR HAVING THE SAME

(75) Inventor: Isamu Takehara, Chiba (JP)

(73) Assignee: Seiko Seiki Kabushiki Kaisha (JP)

( * ) Notice: Subject to any disclaimer, the term of this patent is extended or adjusted under 35 U.S.C. 154(b) by 47 days.

(21) Appl. No.: 09/703,145

(22) Filed: Oct. 31, 2000

Related U.S. Application Data

(62) Division of application No. 08/964,589, filed on Nov. 5, 1997, now Pat. No. 6,163,952.

(30) Foreign Application Priority Data

Nov. 6, 1996 (JP) .............................................. 8-310201

(51) Int. Cl.$^7$ .............................................. H02K 15/02
(52) U.S. Cl. .................. 29/598; 310/217; 310/254; 310/258; 29/606; 29/607
(58) Field of Search .......................... 29/596, 598, 606, 29/607; 310/217, 218, 254, 258, 194

(56) References Cited

U.S. PATENT DOCUMENTS

| | | | | |
|---|---|---|---|---|
| 3,914,859 A | * | 10/1975 | Pierson | 29/596 |
| 4,182,026 A | * | 1/1980 | Searle | 29/596 |
| 5,005,281 A | * | 4/1991 | Burns | 29/596 |
| 5,265,323 A | * | 11/1993 | Odell | 29/596 |
| 5,502,341 A | * | 3/1996 | Sato | 29/596 |
| 5,570,503 A | * | 11/1996 | Stokes | 29/596 |
| 5,722,152 A | * | 3/1998 | Sumi et al. | 29/596 |
| 5,918,360 A | * | 7/1999 | Forbes et al. | 29/596 |

* cited by examiner

*Primary Examiner*—Gregory Vidovich
*Assistant Examiner*—Stephen Kenny
(74) *Attorney, Agent, or Firm*—Adams & Wilks

(57) ABSTRACT

A motor armature which allows assembly works to be facilitated and which can be miniaturized and thinned is provided. An inner cylinder 1 and an outer cylinder 2 are disposed coaxially and a plurality of pole pieces 3 are provided radially at equal intervals between the inner cylinder 1 and the outer cylinder 2. The inner cylinder 1 is formed into a cylindrical shape by curling up in the longitudinal direction a hoop member (band steel) made of a magnetic material and having a predetermined thickness and length. The outer cylinder 2 is made of the hoop member similarly to the inner cylinder 1. The pole piece 3 is what a coil 4 is wound around a wire piece 5 obtained by cutting a wire (wire rod) made of a magnetic material and having a predetermined thickness into a predetermined length. One end of the wire piece 5 is fixed to the outer peripheral face of the inner cylinder 1 by means of welding or the like and the other end of the wire piece is fixed to the inner peripheral face of the outer cylinder 2.

20 Claims, 12 Drawing Sheets

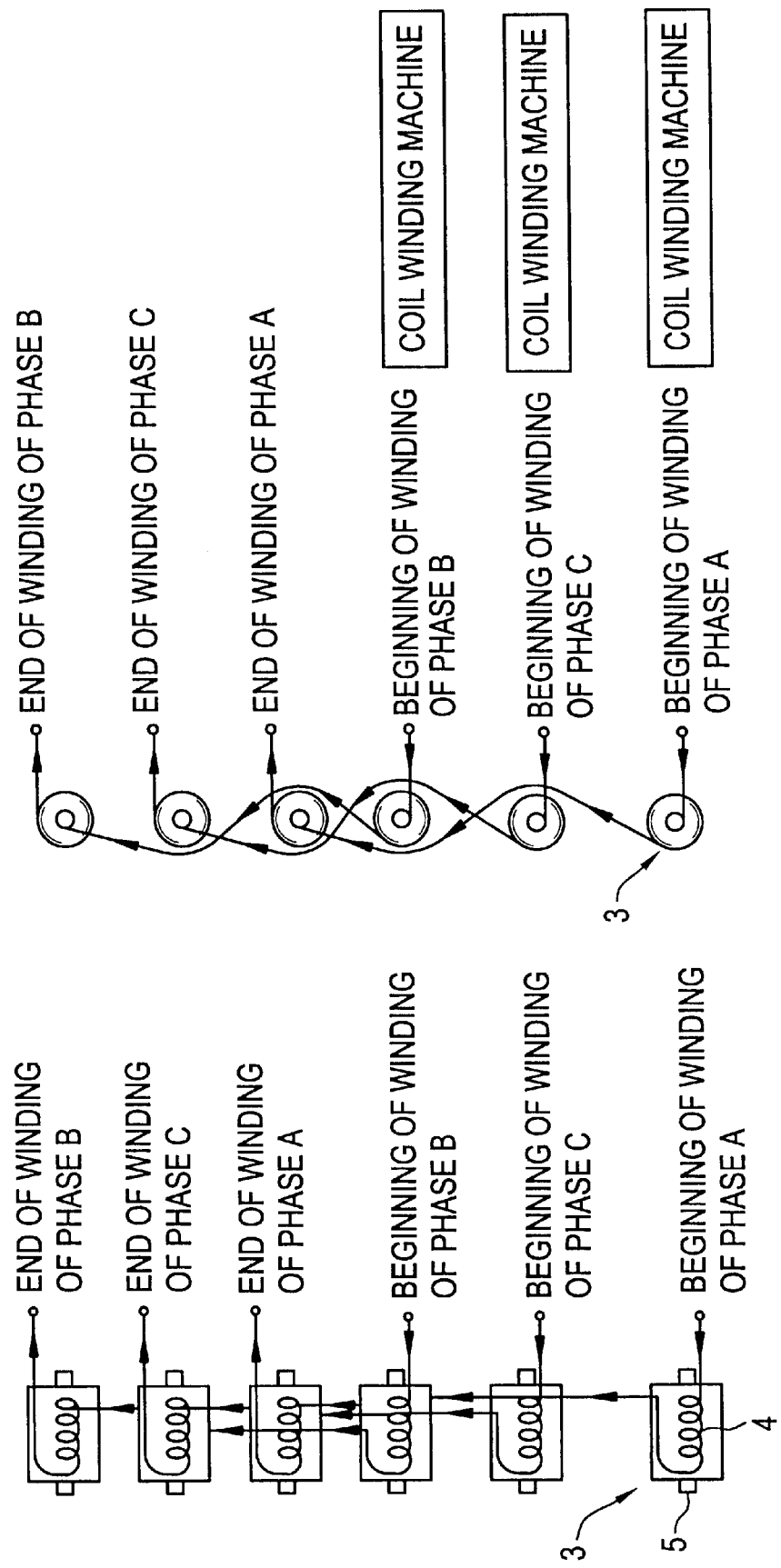

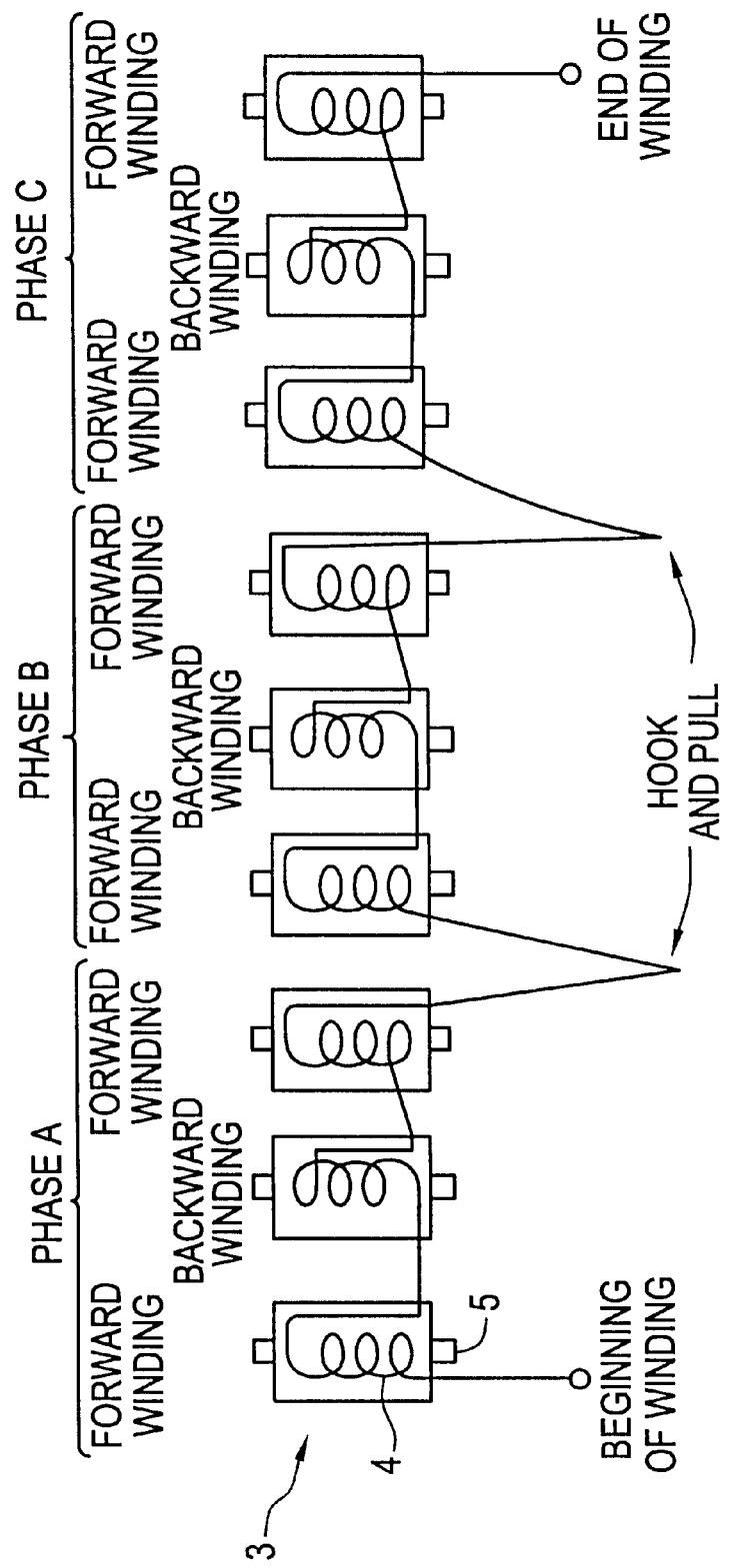

ARMATURE OF MOTOR, MANUFACTURING METHOD OF THE SAME AND MOTOR USING THE SAME AND MOTOR HAVING THE SAME

The present application is a divisional application based on prior U.S. application Ser. No. 08/964,589, filed on Nov. 5, 1997, now U.S. Pat No. 6,163,952 which is hereby incorporated by reference, and priority thereto for common subject matter is hereby claimed.

BACKGROUND OF THE INVENTION

1. [Field of the Invention]

The present invention relates to a motor armature used in motors such as a brushless motor, a manufacturing method thereof and a motor.

2. [Prior Art]

Hitherto, as an armature used for a brushless motor and the like, there have been known one fabricated by winding a coil around an iron core made by laminating a plurality of punched steel plates or one fabricated by winding a coil around an iron core made by laminating a plurality of punched steel plates which are divided into a plurality of pieces and by cylindrically connecting each core around which the coil is wound.

However, the armature fabricated by winding the coil around the iron core made by laminating a plurality of punched steel plates has had problems that its overall structure is complicated in general and that it is difficult to wind the coil around the core.

Meanwhile, the armature fabricated by winding the coil around the iron core made by laminating a plurality of punched steel plates which are divided into a plurality of pieces and by cylindrically connecting each core around which the coil is wound has had a problem that although it is easy to wind the coil around the core, the assembly work thereof for connecting cylindrically each core piece around which the coil is wound is difficult.

SUMMARY OF THE INVENTION

Accordingly, it is a primary object of the present invention to provide a motor armature whose assembly work can be facilitated and which can be miniaturized and thinned.

A secondary object of the present invention is to provide manufacturing methods of the armature which facilitate and readily automate the assembly work.

In order to achieve the primary object, a motor armature of the present invention comprises a plurality of pole pieces in which a coil is wound around a rod made of a magnetic material; and a cylinder made of a magnetic material which is fixed with the plurality of pole pieces disposed radially at equal intervals at the position distant from the center by a predetermined distance on at least one side of the center side or the outer periphery side thereof.

The above-mentioned cylinder is formed by curling up a hoop member made of a magnetic material and the rod is a wire piece obtained by cutting a wire made of a magnetic material.

Because the armature of the present invention is simply constructed as described above, it allows the assembly works to be facilitated and the miniaturization, thinning and reduction of cost to be realized. Further, it allows to deal with changes in the size and structure of the armature readily and swiftly.

In order to achieve the secondary object, a method for manufacturing the inventive motor armature comprises a first step of creating a plurality of pole pieces in which a coil is wound around a wire piece 5 made of a magnetic material; a second step of fixing one end of the plurality of pole pieces created in the first step to one and the same plane of a hoop member made of a magnetic material at equal intervals; and a third step of creating a cylinder attached with pole pieces by curling up the hoop member to which the plurality of pole pieces are fixed in the second step so that the plurality of pole pieces come inside or outside.

Further, in parallel with creating the cylinder attached with the pole pieces by curling up the hoop member to which the plurality of pole pieces are attached so that the plurality of pole pieces come outside in the third step described above, an outer cylinder may be created while fixing each other end of the pole pieces with the hoop member.

Further, an inventive method for manufacturing the motor armature comprises a first step of creating a plurality of pole pieces in which a coil is wound around a wire piece made of a magnetic material; and a second step of fixing one end of the plurality of pole pieces created in the first step either to the inner peripheral face or the outer peripheral face of a cylinder formed by curling up a hoop member made of a magnetic material radially at equal intervals.

Further, in the second step described above, it is possible to arrange such that an outer cylinder coaxial with the cylinder attached with the pole pieces is fixed with other end of the plurality of pole pieces fixed to the cylinder attached with the pole pieces after creating the cylinder attached with the pole pieces by curling up the hoop member so that the plurality of pole pieces come outside.

Thus, the rod (wire piece) and the hoop members are used in the inventive method for manufacturing the armature. It then allows the automation to be facilitated and to deal with changes in the size and structure of the armature swiftly by changing the thickness of the wire piece and the thickness of the hoop member.

BRIEF DESCRIPTION OF DRAWINGS

FIG. 8 is a drawing showing a method for creating the pole piece.

FIG. 9 is a drawing showing another method for creating the pole piece.

DESCRIPTION OF THE PREFERRED EMBODIMENT(S)

Preferred modes of a motor armature of the invention and its manufacturing methods will be explained below in detail with reference to FIGS. 1 through 13.

Figure 1:
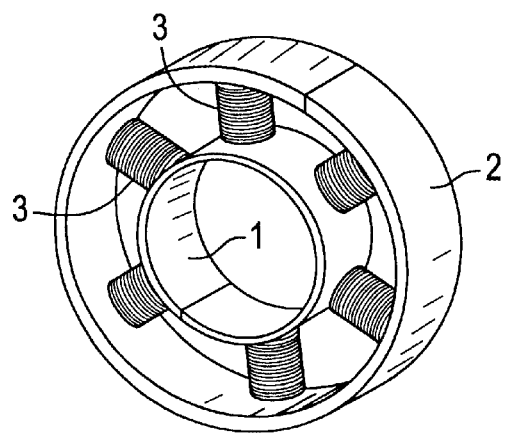
FIG. 1 is a perspective view showing a mode of an armature of the present invention.

FIG. 1 is a perspective view of the armature according to the mode.

As shown in FIG. 1, this armature is constructed by disposing coaxially an inner cylinder 1 and an outer cylinder 2 and by providing a plurality of pole pieces 3 radially at equal intervals between the inner cylinder 1 and the outer cylinder 2.

The inner cylinder 1 is formed into the cylinder shape by curling up in the longitudinal direction a hoop member (band steel) which is made of a magnetic material and which has a predetermined thickness and length and by jointing the both ends thereof by welding or the like.

Similarly to the inner cylinder 1, the outer cylinder 2 is formed into the cylinder shape by curling up in the longitudinal direction a hoop member (band steel) which is made of a magnetic material and which has a predetermined thickness and length and by jointing the both ends thereof by welding or the like.

Figure 2:
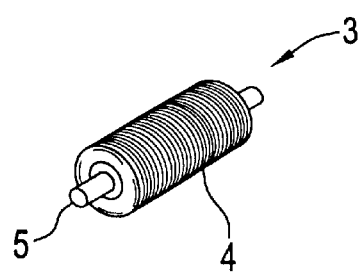
FIG. 2 is a perspective view showing a structure of a pole piece.

As shown in FIG. 2, the pole piece 3 consists of a wire piece 5 obtained by cutting a wire (wire rod) which is made of a magnetic material and which has a predetermined thickness into a predetermined length and a coil 5 wound around the wire piece 5. One end of the wire piece 5 is fixed to the outer peripheral face of the inner cylinder 1 by welding or the like and the other end of the wire piece 5 is fixed to the inner peripheral face of the outer cylinder 2.

While the plurality of pole pieces 3 are provided between the inner cylinder 1 and the outer cylinder 2, the number thereof is determined depending on a design and specifications of a motor, like three, six, eight, nine or twelve.

Because the wire piece 5 is obtained by cutting a wire and its shape of section is the same (circular) in the longitudinal direction, there is a merit that the coil 4 can be readily wound by a coil winding machine. However, the shape of the wire piece 5 is not limited only to such shape, and it is possible to provide fixing sections like convex sections at the both ends thereof so as to insert the convex sections to fixing holes provided on the inner cylinder 1 and the outer cylinder 2.

Further, the sectional shape of the wire piece 5 in the longitudinal direction is not limited to be circular, and it may be triangular or square. Still more, the wire piece 5 may be formed by laminating thin plate-like members.

Figure 3:
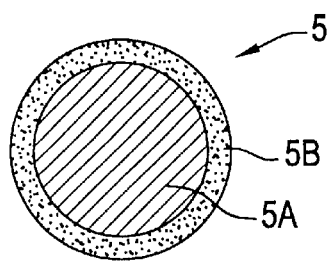
FIG. 3 is a section view showing a section of a wire piece.

Next, the internal structure of the wire piece 5 will be explained with reference to FIG. 3.

The wire piece 5 is composed of a center layer 5A whose section is circular and a skin layer 5B which is formed so as to have a constant thickness around the center layer 5A.

The center layer 5A is made of low carbon steel or pure iron which are magnetic materials having high saturation magnetic flux density. The skin layer 5B is made of Fe—Co alloy, Fe—Ni alloy or amorphous alloy which are magnetic materials having high magnetic permeability and causing less iron loss. The reason why the wire piece 5 is composed of the two layers, using the magnetic materials having different natures, will be explained below.

Figure 4:
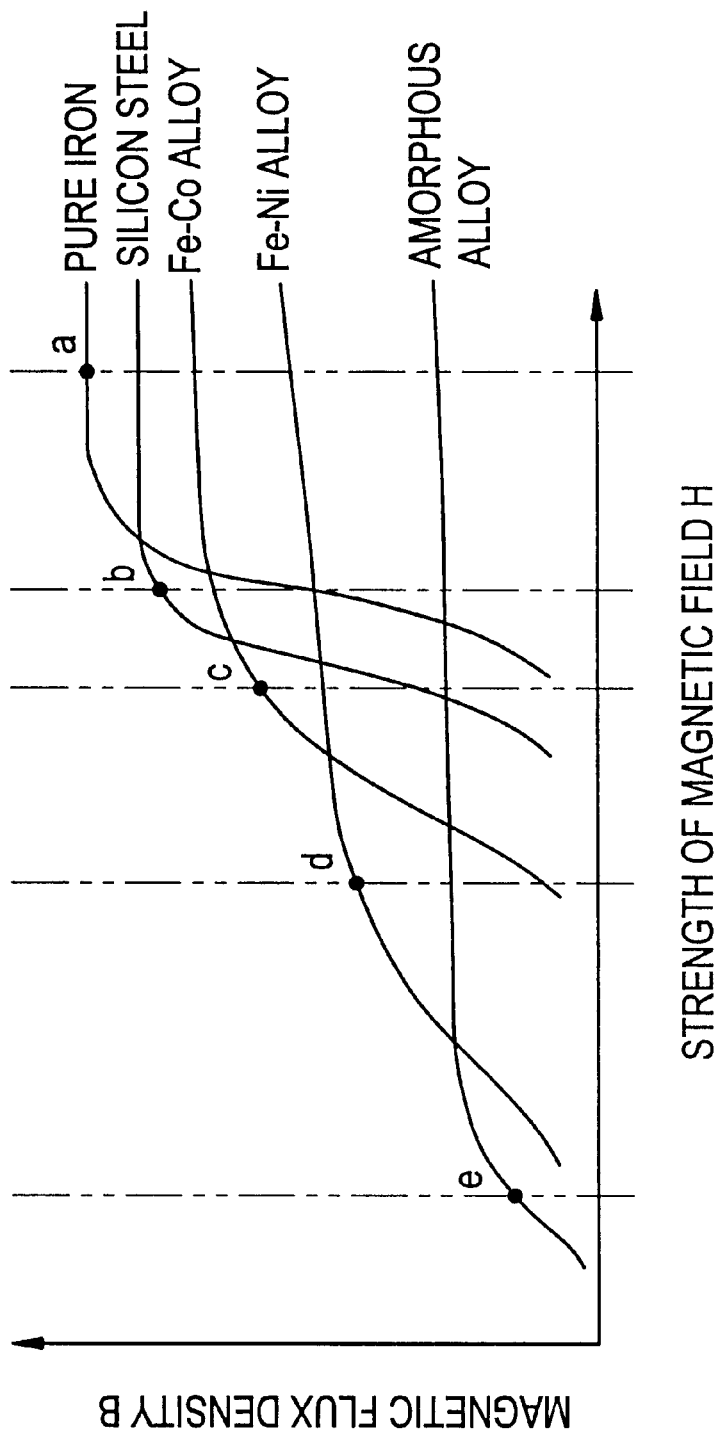
FIG. 4 is a magnetic characteristic chart of magnetic materials.
Figure 5:
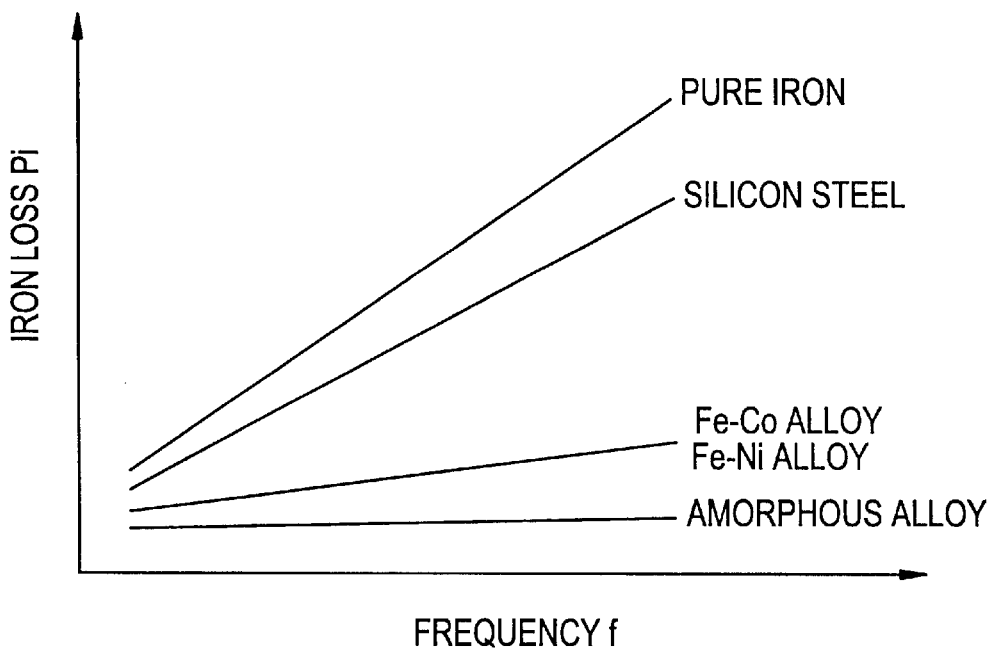
FIG. 5 is a frequency characteristic chart of the magnetic materials.
Figure 6:
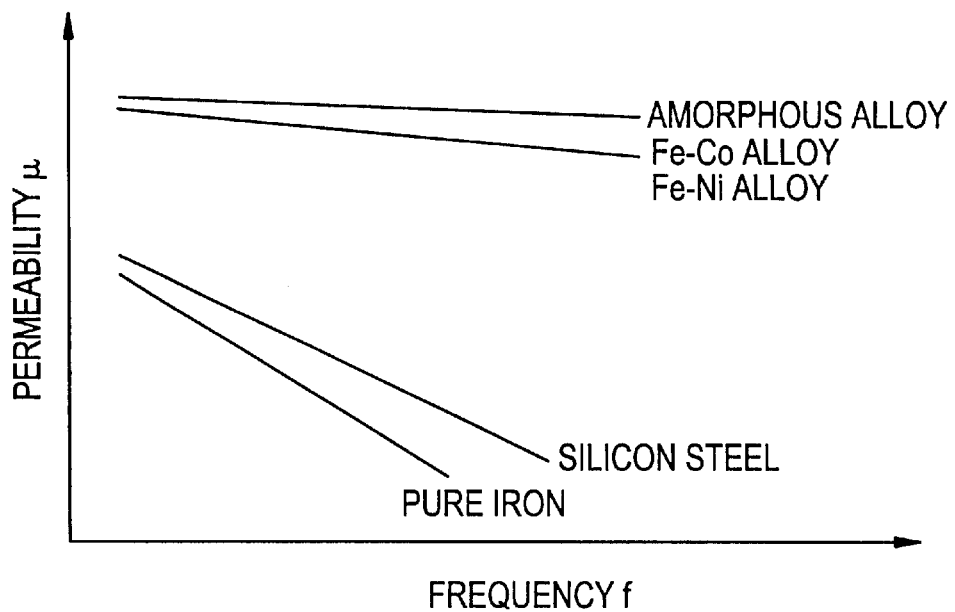
FIG. 6 is a frequency characteristic chart of permeability.

FIG. 4 is a magnetic characteristic chart of various magnetic materials. FIG. 5 is a frequency characteristic chart of iron loss the magnetic materials. FIG. 6 is a frequency characteristic chart of permeability of the magnetic materials. According to FIG. 4, when the strength of magnetic field is determined in order of a, b, c, d and e, the flux density corresponding to that is determined accordingly.

When the armature of the present mode is used in a motor, there is no big difference in the iron loss of the various magnetic materials in activating the motor because alternating frequency is low as shown in FIG. 5. Accordingly, the pure iron and silicon steel which can be readily worked are suited. Further, because a large torque is required in activating the motor and a large current flows through the coil, increasing the strength of the magnetic field, the pure iron and the silicon steel which are the magnetic materials having the high saturation magnetic flux density as shown in FIG. 4 are suited.

When the motor rotates at high speed after the activation on the other hand, the alternating frequency of the magnetic flux becomes high. In this case, although the iron loss of the pure iron and the like increases remarkably in correspondence to the increase of the frequency, the iron loss of the amorphous alloy and the like does not increase so much in correspondence to the increase of the frequency, the Fe—Co alloy, Fe—Ni alloy or amorphous alloy is suited. Further, as the strength of the magnetic field is reduced because the current flowing through the coil decreases during the high speed rotation of the motor after the activation, the one having relatively high saturation magnetic flux density is suited, even though the strength of the magnetic field is small like the Fe—Co alloy, Fe—Ni alloy or amorphous alloy as shown in FIG. 4.

Thus, the magnetic materials suited as the wire piece 5 are mutually contradictory in activating the motor and in rotating it at high speed after the activation and it is difficult to cover the whole range from the activation to the high speed rotation of the motor by either one of the magnetic materials. Therefore, it is conceivable to combine the two materials having the different natures.

By the way, during the high speed rotation of the motor after the activation, the alternating frequency of the magnetic flux is high so that it causes a skin effect of the magnetic flux. As result of it, the magnetic flux density of the wire piece 5 on the skin side increases so that the wire piece 5 is caused less iron loss at the center side thereof and caused large iron loss at the skin side thereof.

Accordingly, it is preferable to make the skin side of the wire piece 5 by the Fe—Co alloy, Fe—Ni alloy or amorphous alloy which causes less iron loss even when the frequency is high as shown in FIG. 5 in order to minimize the large iron loss at the skin side caused by the skin effect.

Then, it is preferable to make the center layer 5A of the wire piece 5 by the low carbon steel or pure iron which are the magnetic materials having high saturation magnetic flux density and to make the skin layer 5B by the Fe—Co alloy, Fe—Ni alloy or amorphous alloy which are the magnetic materials having high magnetic permeability and causing less iron loss.

By composing the wire piece 5 as described above, a loss caused by the iron loss may be reduced across the whole range from the activation to the high speed rotation of the motor. It also allows a magnetic flux necessary for driving to be obtained mainly by the center layer 5A part in activating the motor and a magnetic flux necessary for rotation to be obtained mainly by the skin part 5A in rotating the motor at high speed.

Further, the iron loss caused by the skin effect of the magnetic flux may be reduced even if a number of rotation of the motor is increased from several thousands rpm to ten thousands rpm by composing the wire piece 5 as described above.

The armature of the present mode constructed as described above may be used by combining either an inner rotor or an outer rotor made of permanent magnet for example.

Further, the armature of the present invention may be what only the outer cylinder 2 is removed from the armature shown in FIG. 1 (armature which is composed of the pole pieces 3 and the inner cylinder 1). In this case, it is used by combining with the outer rotor.

Still more, the armature of the present invention may be what the inner cylinder 1 is removed from the armature shown in FIG. 1 (armature which is composed of the pole pieces 3 and the outer cylinder 2). In this case, it is used by combining with the inner rotor.

Methods for manufacturing the armature constructed as described above will be explained below.

FIG. 7 is a process drawing for explaining a first method for manufacturing the armature.

Figure 7A:
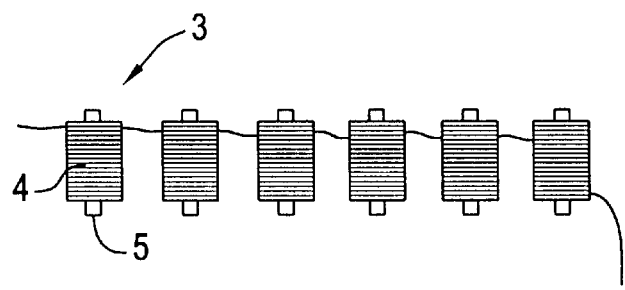
FIG. 7 is a drawing showing steps of a first method for manufacturing of the armature.

In the first manufacturing method, the coil 4 is wound as described later around the wire pieces 5 which are obtained by cutting a wire made of a magnetic material into a predetermined length to create the plurality of pole pieces 3 as shown in FIG. 7(A). Here, six pole pieces 3 are created.

Figure 7B:
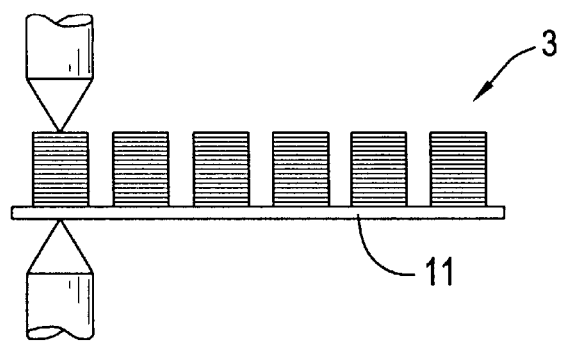

Next, one end of the wire piece 5 of the plurality of pole pieces 3 is fixed to a hoop member 11 which has been cut into a predetermined length beforehand at equal intervals by joint means such as spot welding or caulking as shown in FIG. 7(B).

Figure 7C:
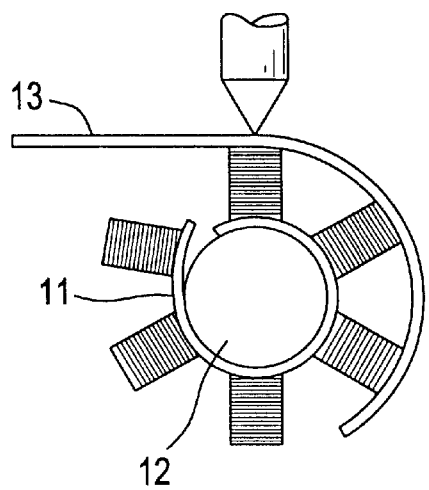

Then, in parallel with creating the inner cylinder by winding the hoop member 11 around a core 12, each of the other end of the wire piece 5 of the pole pieces 3 is fixed to a hoop member 13 by means of spot welding or caulking to create the outer cylinder as shown in FIG. 7(C). Then, the armature as shown in FIG. 1 is completed.

It is noted that in FIG. 7(C), the inner cylinder may be created in advance by curling up the hoop member 11 on which the pole pieces 3 are fixed and the outer cylinder maybe created thereafter by curling up the hoop member 13 as described above.

It is noted that although the pole piece 3 is created by winding the coil 4 around the wire piece 5 which has been cut in advance in FIG. 7(A), it is also possible, instead of that, to wind the coil 4 at the edge of the continuous wire in advance and to cut the wire into the length of the wire piece 5 after winding the coil 4.

Further, although the one end of the pole piece 3 is fixed to the hoop member 11 which has been cut in advance in FIG. 7(B), it is also possible, instead of that, to fix one end of the plurality of pole pieces 3 to the hoop member 11 and to cut the hoop member after finishing the fixation.

Next, a method for creating the pole pieces 3 by winding the coil around the wire piece explained in FIG. 7(A) will be explained.

FIG. 8 is a drawing diagrammatically showing a case of creating a three-phase coil by using three coil winding machines. In this case, the winding directions of the six pole pieces are all the same. Then, star connection or delta connection is made after that.

FIG. 9 is a drawing diagrammatically showing a case of creating the three-phase coil by using one coil winding machine. In this case, the three poles of each phase of A, B and C are wound forward, backward and forward. A delta connection is made by hooking two spots to connect the beginning and the end of the winding as shown in FIG. 9.

Figure 10:
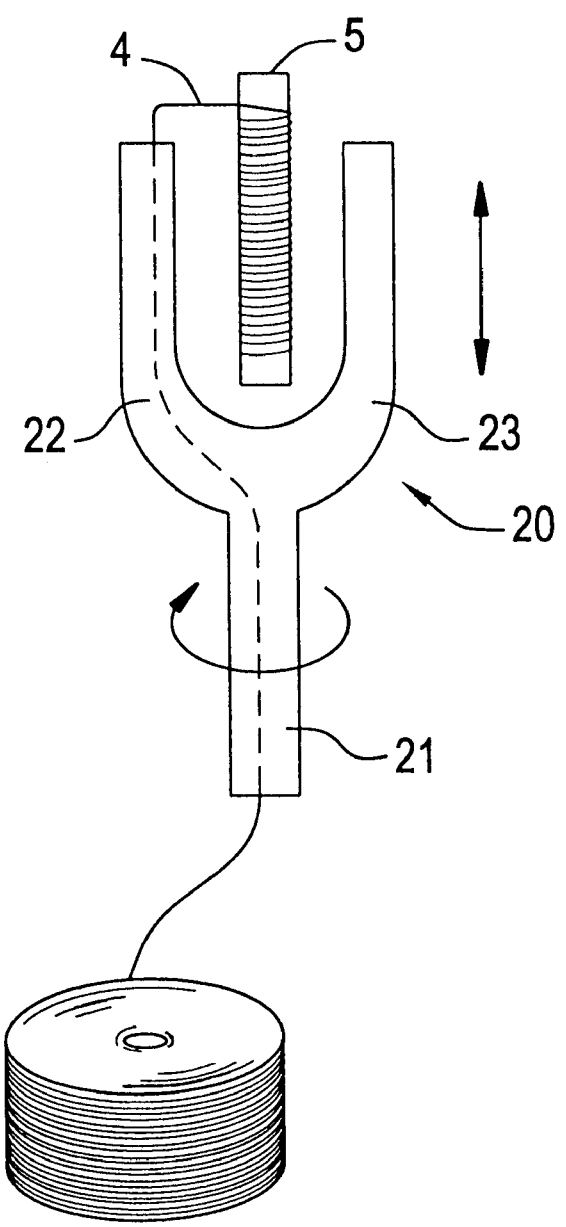
FIG. 10 is a drawing diagrammatically showing a coil winding machine.

FIG. 10 is a drawing diagrammatically showing a coil winder 20 for winding the coil 4 around the wire piece 5. This coil winder 20 comprises a cylindrical base 21, a cylindrical winding section 22 which continues therefrom and bifurcates to the left side of the figure and a balance section 23 which bifurcates to the right side of the figure. It is constructed so that the whole of it moves forward and back while turning.

In winding the coil 4 around the wire piece 5, the coil 4 is discharged from an opening at the edge of the winding section 22 via the base 21 and the winding section 22 and the whole coil winder 20 moves forward or back while turning. Thereby, the discharged coil 4 is wound around the wire piece 5. It is noted that the balance section 23 takes a balance when the winding section 22 turns.

By the way, a number of rotation of the coil winding machine is around 3000 rpm at most in winding a coil around a prior art armature by means of the special coil winding machine because the structure of the armature is complicated.

However, the wire piece 5 of the present mode is a rod whose section is circular in the longitudinal direction, there is a merit that the number of rotation of the coil winding machine may be increased up to 50,000 to 60,000 rpm in winding the coil 4 by the above-mentioned coil winding machine.

Next, a second method for manufacturing the armature will be explained with reference to process drawings shown in FIG. 11.

Figure 11A:
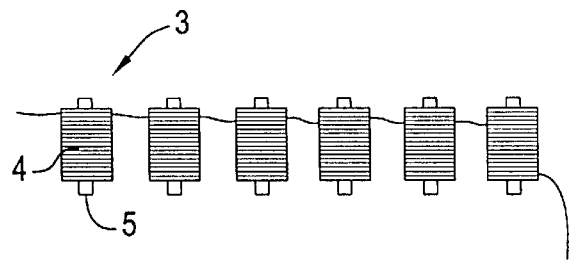
FIG. 11 is a drawing showing steps of a second method for manufacturing of the armature.
Figure 11B:
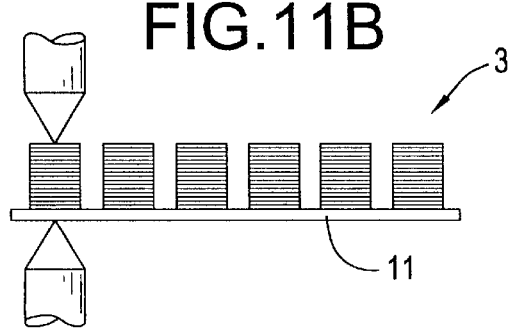

The second manufacturing method is the same with the first manufacturing method up to the steps of creating the plurality of pole pieces 3 in which the coil 4 is wound around the wire piece 5 and of fixing one end of the wire piece 5 of the plurality of pole pieces 3 to the hoop member 11 at equal intervals (see FIGS. 11(A) and 11(B)).

Figure 11C:
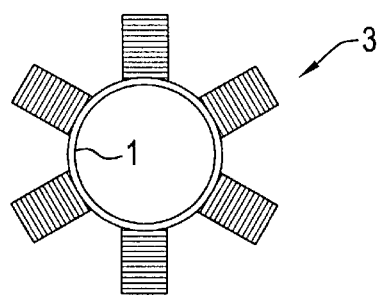

Next, when the hoop member 11 is curled up by winding around the core and the both ends thereof are jointed by welding or the like, the inner cylinder 1 on which the pole pieces 3 are disposed radially is created as shown in FIG. 11(C).

Figure 11D:
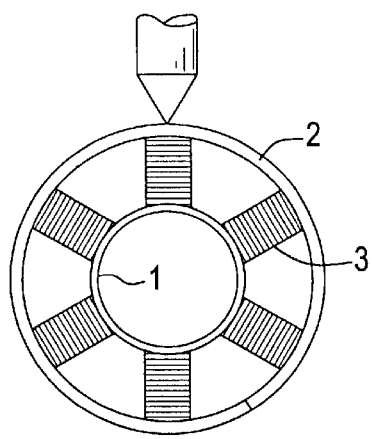

Then, when the outer cylinder 2 made of the hoop member is disposed coaxially with the inner cylinder 1 as shown in FIG. 11(D), the inner peripheral face of the outer cylinder 2 contacts with each other end of the wire piece of the pole piece 3. Each other end of each wire piece is then jointed with the inner peripheral face thereof by means of spot welding or the like, thus completing the armature as shown in FIG. 1.

The armature thus created by the second manufacturing method may be used in combination either with an inner rotor or an outer rotor. The armature in the state in FIG. 11(C) may be used in combination with the outer rotor.

Next, a third method for manufacturing the armature will be explained with reference to process drawings shown in FIG. 12.

Figure 12A:
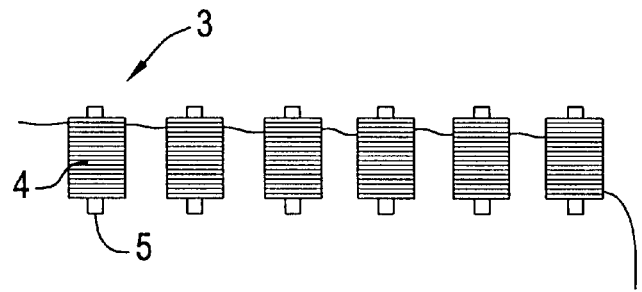
FIG. 12 is a drawing showing steps of a third method for manufacturing of the armature.
Figure 12B:
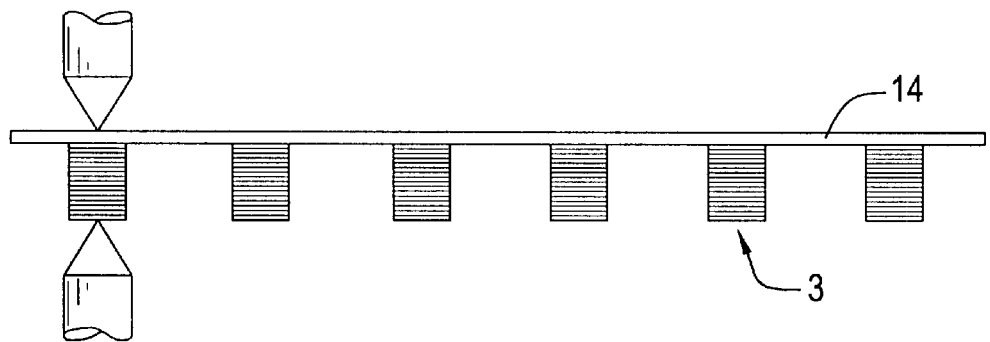

The third manufacturing method is the same with the first manufacturing method up to the steps of creating the plurality of pole pieces 3 in which the coil 4 is wound around the wire piece 5 and of fixing one end of the wire piece 5 of the plurality of pole pieces 3 at equal intervals to a hoop member 14 cut into a predetermined length in advance (see FIGS. 12(A) and 12(B)).

Figure 12C:
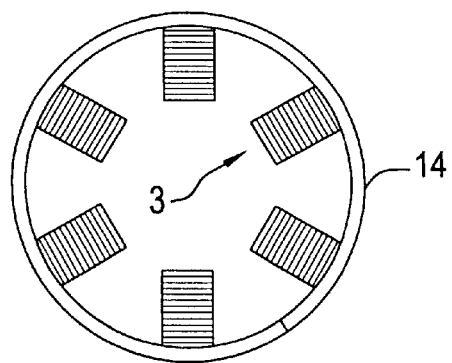

Next, when the hoop member 14 is curled up by winding around the core so that each pole piece 3 comes inside and the both ends thereof are jointed by welding or the like, a cylinder in which the pole pieces 3 are fixed so as to head the center is created as shown in FIG. 12(C). Thus, the armature which can be used in combination with the inner rotor is completed.

Next, a fourth method for manufacturing the armature will be explained with reference to process drawings shown in FIG. 13.

Figure 13A:
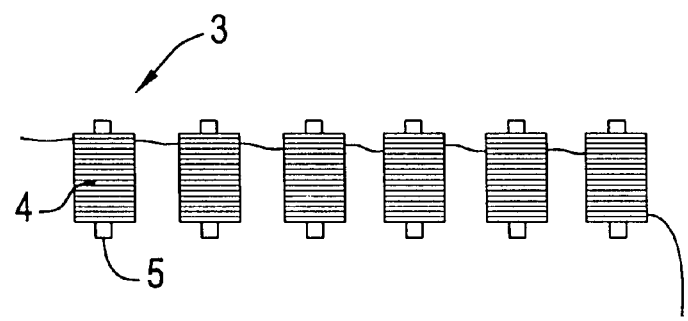
FIG. 13 is a drawing showing steps of a fourth method for manufacturing of the armature.

The fourth manufacturing method is the same with the first manufacturing method up to the step of creating the plurality of pole pieces 3 in which the coil 4 is wound around the wire piece 5 (see FIG. 13(A)).

Figure 13B:
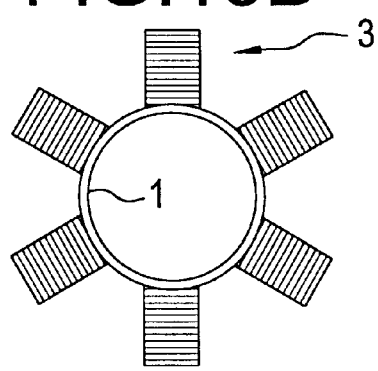

Next, one end of the wire piece 5 of the plurality of pole pieces 3 is fixed radially at equal intervals to the outer peripheral face of the inner cylinder 1 formed by curling up the hoop member as shown in FIG. 13(B) by means of spot welding or caulking.

Figure 13C:
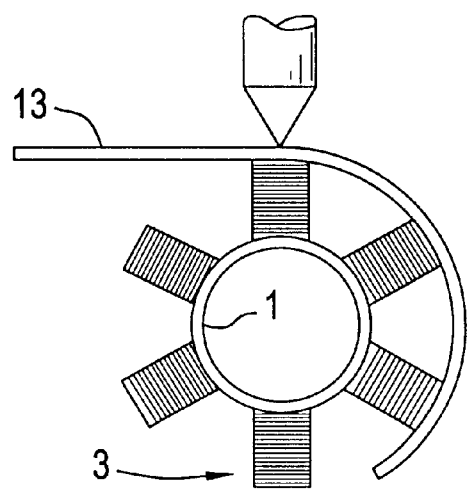

Next, as shown in FIG. 13(C), when the outer cylinder is formed while fixing each other end of the wire piece 5 of the pole piece 3 to the hoop member 13 by means of spot welding or caulking, the armature as shown in FIG. 1 is completed.

It is noted that the plurality of pole pieces 3 in which the coil 4 is wound around the wire piece 5 are created and the wire piece 5 of the plurality of pole pieces 3 are fixed to the outer peripheral face of the inner cylinder 1 which has been formed by curling up the hoop member in the fourth method.

However, it is also possible to create the armature in the state of FIG. 13(B) by fixing the plurality of wire pieces 5 to the hoop member in advance at equal intervals, by creating the inner cylinder 1 by curling up the hoop member on which the wire pieces 5 are fixed and by winding the coil 4 to each wire piece 5 fixed to the inner cylinder 1 at equal intervals.

Next, a fifth method for manufacturing the armature will be explained with reference to process drawings shown in FIG. 14.

Figure 14A:
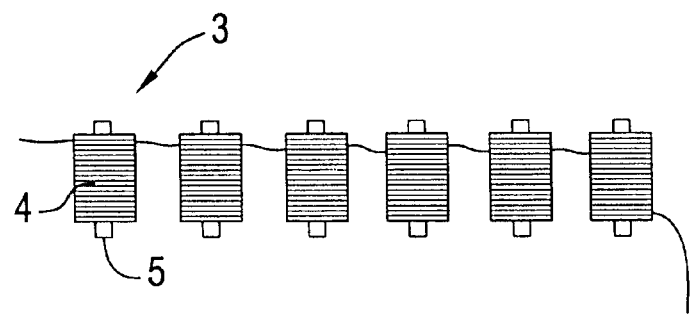
FIG. 14 is a drawing showing steps of a fifth method for manufacturing of the armature.

The fifth manufacturing method is the same with the fourth manufacturing method up to the step of creating the plurality of pole pieces 3 in which the coil 4 is wound around the wire piece 5 (see FIG. 14(A)).

Figure 14B:
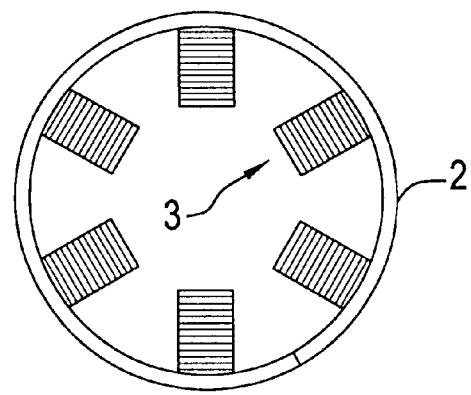

Next, one end of the wire piece 5 of each pole piece 3 is jointed to the inner peripheral face of the outer cylinder 2 created by curling up the hoop member so that each pole piece 3 heads the center by means of spot welding or caulking as shown in FIG. 14(B).

Figure 14C:
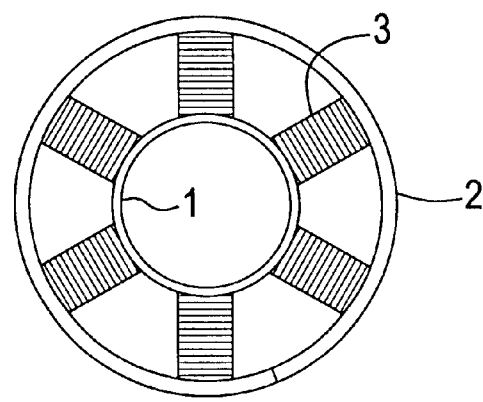

Next, when the inner cylinder 1 made of the hoop member is disposed coaxially with the outer cylinder 2 as shown in FIG. 14 (C), the outer peripheral face of the inner cylinder 1 contacts with each other end of the wire piece of the pole piece 3. Then, each other end of each wire piece is jointed with the outer peripheral face by means of spot welding or caulking, thus completing the armature as shown in FIG. 1.

Figure 15:
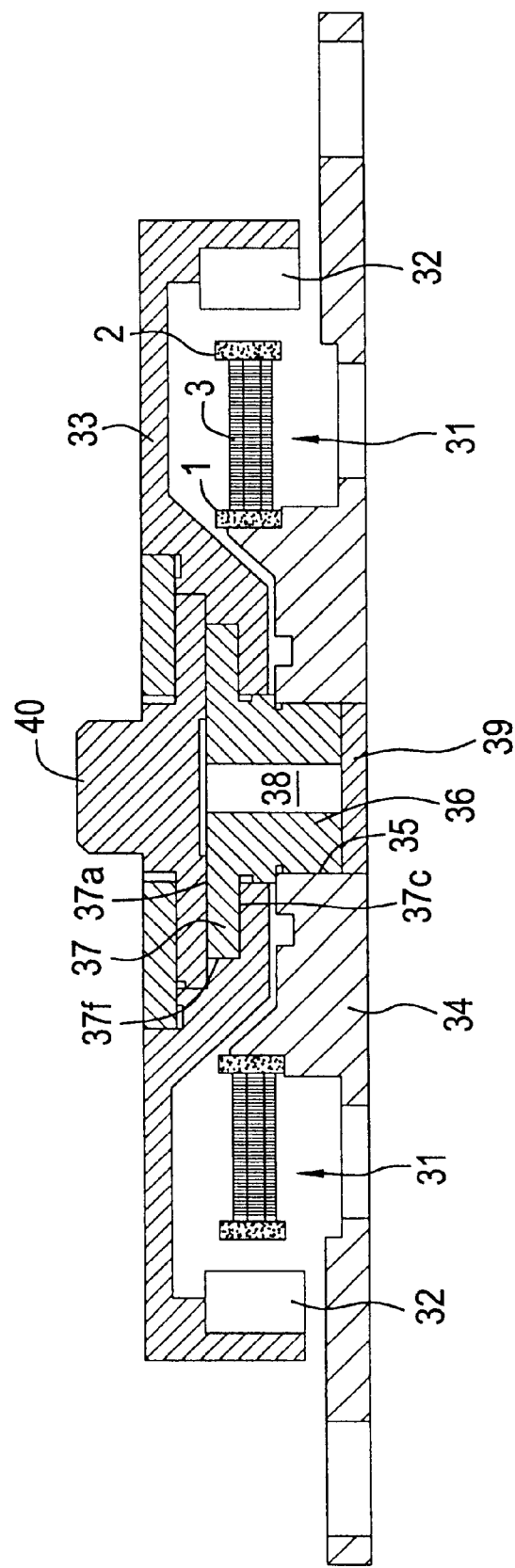
FIG. 15 is a section view showing a spindle motor having a motor armature as shown in FIG. 1.

FIG. 15 is a sectional view of a high speed spindle motor using a motor armature shown in FIG. 1.

a stator 31 which is formed by winding wirings around an iron core, namely, a motor armature is mounted at a position facing the magnet 32 mounted on the inner circumferential surface of the bottomed rotor 33 on the outer circumferential side of the stationary base 34.

In this embodiment, there is provided a stationary basell.

A central hole 35 is formed at the center of the stationary basell a lower portion of cylindrical stationary shaft 36 is press-fitted into the central hole 35.

A central hole 35 is formed at the center of the stationary base 34. A lower portion of a cylindrical stationary shaft 13 is press-fitted into the central hole 35.

As shown in FIGS. 15, a flange disc 37 for the bearing is provided coaxially with the stationary shaft 36 in the upper portion of the stationary shaft 36. Although this flange disc 15 is formed integrally with the stationary shaft 36, instead thereof, the flange disc 37 may be formed discretely from the stationary shaft 36 and may be coupled therewith by a suitable means.

An oil feed hole 38 for feeding oil is provided in the axial direction of the inner central portion of the stationary shaft 36. An opening of the oil feed hole 38 may be covered by a sealing cover 39 after the replenishment of the oil.

An outer circumferential surface of the flange disc 37 is formed as a radial dynamic pressure bearing portion 37$f$ for supporting in the radial direction the rotary member composed of a bottomed rotor 33 and a thrust retaining portion 40.

The top surface and the bottom surface of the flange disc 37 are formed into thrust dynamic pressure bearing portions 37$a$ and 37$c$, respectively, for supporting in the axial direction the rotary member composed of the bottomed rotary 33 and the thrust retaining portion 40.

Because the armature of the present invention is structured as described above, the assembly works can be facilitated, it can be miniaturized and thinned and its cost can be reduced. In addition to that, it allows to deal with changes in size and structure thereof flexibly when there is such change.

Further, because the rod (wire piece) and the hoop members are used in the manufacturing methods of the inventive armature, it facilitates the automation and allows to deal with changes in size and structure of the armature swiftly where there is such change by changing the thickness of the wire piece or the thickness of the hoop member.

What is claimed is:

1. A motor armature, comprising:
    a plurality of pole pieces each comprising a coil wound around a rod formed of a magnetic material; and
    a cylinder made of a magnetic material fixed to the plurality of pole pieces so that the pole pieces are disposed radially at equal intervals at a position distant from the center of the cylinder by a predetermined distance on at least one of an inner and outer peripheral surface of the cylinder, the cylinder being comprised of a hoop member made of a magnetic material curled into a cylinder, and the rod being comprised of a wire piece formed by cutting a wire made of a magnetic material.

2. A motor armature according to claim 1; wherein one end of each of the pole pieces is welded to a first surface of the hoop member such that the pole pieces are spaced by equal intervals.

3. A motor armature according to claim 1; wherein the hoop member comprises a flat sheet curled up into a cylinder so that the plurality of pole pieces are fixed to the inside or outside of the cylinder.

4. A motor armature according to claim 1; further comprising an outer cylinder coaxial with the inner cylinder and attached to an end of each of the pole pieces.

5. A motor armature according to claim 1; wherein the rod of each of the pole pieces comprises an inner core formed of a magnetic material having a high saturation magnetic flux density and a skin layer formed around the inner core comprising a magnetic material having a lower saturation magnetic flux density than the core and having higher magnetic permeability than the core, so that the pole pieces formed from the magnetic wire rod undergo a low iron loss when used in the motor.

6. A motor armature according to claim 5, wherein the inner core comprises one of low carbon steel and pure iron.

7. A motor armature according to claim 6; wherein the inner core comprises one of low carbon steel and pure iron.

8. A motor armature according to claim 6; wherein the skin layer comprises one of Fe—Co alloy, Fe—Ni alloy and amorphous alloy.

9. A motor armature according to claim 6; wherein the wire piece has a circular cross section.

10. A motor armature according to claim 6; wherein the plurality of pole pieces comprise a magnetic wire rod cut into a plurality of pieces, and a plurality of wires formed of a magnetic material wound around selected pieces of the magnetic wire, so that each piece has a coil formed of a single wire wound therearound, to form a multi-phase armature.

11. A motor armature according to claim 5; wherein the skin layer comprises one of Fe—Co alloy, Fe—Ni alloy and amorphous alloy.

12. A motor armature according to claim 5; wherein the wire piece has a circular cross section.

13. A motor armature according to claim 1; wherein the plurality of pole pieces comprise a magnetic wire rod cut into a plurality of pieces, and a plurality of wires formed of a magnetic material wound around selected pieces of the magnetic wire, so that each piece has a coil formed of a single wire wound therearound, to form a multi-phase armature.

14. A motor armature comprising:
a plurality of pole pieces each comprising a coil wound around a rod formed of a magnetic material;
an inner cylinder formed of a magnetic material and having an outer peripheral surface fixed to a first end of the plurality of pole pieces so that the pole pieces are disposed radially at equal intervals outside the inner cylinder; and
an outer cylinder fixed to a second end of each of the pole pieces so that the pole pieces are disposed radially at equal intervals to an inner peripheral surface of the outer cylinder, each cylinder being comprised of a hoop member made of a magnetic material curled into a cylinder, and the rod being comprised of a wire piece formed by cutting a wire made of a magnetic material.

15. A motor armature according to claim 14; wherein opposite ends of each of the pole pieces are welded to the hoop members such that the pole pieces are spaced by equal intervals.

16. A motor armature according to claim 14; wherein the hoop members are simultaneously curled up into cylinders.

17. A motor armature according to claim 14; wherein the rod of each of the pole pieces comprises an inner core formed of a magnetic material having a high saturation magnetic flux density and a skin layer formed around the inner core comprising a magnetic material having a lower saturation magnetic flux density than the core and having higher magnetic permeability than the core, so that the pole pieces formed from the magnetic wire rod undergo a low iron loss when used in the motor.

18. A motor armature, comprising:
a plurality of pole pieces each comprising a coil wound around a rod formed of a magnetic material; and
a cylinder made of a magnetic material fixed to the plurality of pole pieces so that the pole pieces are disposed radially at equal intervals at a position distant from the center of the cylinder by a predetermined distance on at least one of an inner and outer peripheral surface of the cylinder; wherein the rod of each of the pole pieces comprises an inner core formed of a magnetic material having a high saturation magnetic flux density and a skin layer formed around the inner core comprising a magnetic material having a lower saturation magnetic flux density than the core and having higher magnetic permeability than the core.

19. A motor armature according to claim 18; wherein the plurality of pole pieces comprise a magnetic wire rod having an inner core formed of a magnetic material having a high saturation magnetic flux density and a skin layer formed around the inner core comprising a magnetic material having a lower saturation magnetic flux density than the core and having higher magnetic permeability than the core, the rod being cut into a plurality of pieces, and a plurality of wires formed of a magnetic material wound around selected pieces of the magnetic wire rod, so that each piece has a coil formed of a single wire wound therearound, to form a multi-phase armature.

20. A motor armature comprising:
a plurality of pole pieces each comprising a coil wound around a rod formed of a magnetic material;
an inner cylinder formed of a magnetic material and having an outer peripheral surface fixed to a first end of the plurality of pole pieces so that the pole pieces are disposed radially at equal intervals outside the inner cylinder; and
an outer cylinder fixed to a second end of each of the pole pieces so that the pole pieces are disposed radially at equal intervals to an inner peripheral surface of the outer cylinder, wherein the rod of each of the pole pieces comprises an inner core formed of a magnetic material having a high saturation magnetic flux density and a skin layer formed around the inner core comprising a magnetic material having a lower saturation magnetic flux density than the core and having higher magnetic permeability than the core.

* * * * *